United States Patent
Hasenberg et al.

(10) Patent No.: US 7,217,843 B2
(45) Date of Patent: May 15, 2007

(54) METHOD OF MAKING 2-THIOLS

(75) Inventors: Daniel M. Hasenberg, Humble, TX (US); Mitchell D. Refvik, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 11/115,775

(22) Filed: Apr. 27, 2005

(65) Prior Publication Data

US 2006/0247475 A1    Nov. 2, 2006

(51) Int. Cl.
*C07C 319/00*    (2006.01)

(52) U.S. Cl. .................. 568/73; 568/72; 568/59; 568/61; 568/69; 568/38

(58) Field of Classification Search .............. 568/73, 568/72, 59, 61, 69, 38
See application file for complete search history.

(56) References Cited

U.S. PATENT DOCUMENTS

| | | | | |
|---|---|---|---|---|
| 2,386,769 A | * | 10/1945 | Badertscher et al. | 568/73 |
| 2,434,510 A | * | 1/1948 | Olin et al. | 568/73 |
| 2,464,049 A | * | 3/1949 | Mikeska | 568/72 |
| 2,502,596 A | * | 4/1950 | Schulze | 568/73 |
| 2,610,981 A | * | 9/1952 | Short | 568/59 |
| 2,951,875 A | * | 9/1960 | Loev et al. | 568/73 |
| 3,963,785 A | | 6/1976 | Kubicek | |
| 4,161,493 A | | 7/1979 | Barrault et al. | |
| 4,582,939 A | * | 4/1986 | Perozzi et al. | 568/72 |
| 4,638,093 A | * | 1/1987 | Fried | 568/73 |

FOREIGN PATENT DOCUMENTS

DE    1238015    * 4/1967

OTHER PUBLICATIONS

2-Pentanethiol MSDS dated Mar. 19, 2002.

* cited by examiner

*Primary Examiner*—Thurman K. Page
*Assistant Examiner*—Chukwuma Nwaonicha
(74) *Attorney, Agent, or Firm*—Kimberly L. Brown

(57) ABSTRACT

A process for selectively making 2-thiols from alpha olefins is described. The process includes contacting a linear or branched alpha olefin having with $H_2S$ in the presence of a catalyst and recovering the 2-thiol from a product mixture. The catalyst includes a support and at least one metal selected from Group IIIA-VIIIA and the branched olefin is branched at the 3-position or higher with respect to the olefin double bond. Compositions wherein the 2-thiols are substantially free of 1-thiol and 3-thiol isomers are also described.

20 Claims, No Drawings

METHOD OF MAKING 2-THIOLS

CROSS REFERENCE TO RELATED APPLICATIONS

Not Applicable.

FEDERALLY SPONSORED RESEARCH

Not Applicable.

REFERENCE TO MICROFICHE APPENDIX

Not Applicable.

FIELD OF THE INVENTION

This invention relates to the manufacture of 2-thiols from alpha olefins and hydrogen sulfide.

BACKGROUND OF THE INVENTION

Mercaptans, also known as thiols, are organic compounds that are used in diverse applications. Some mercaptans are used as agricultural supplements or as polymerization process modifiers. When mercaptans are present in large quantities, they are generally considered to be malodorous and highly undesirable. But in low concentrations these same compounds are used as fragrances and flavorings. When used in this manner they can be an effective and economical replacement of more expensive natural products in a wide variety of perfumed articles such as soaps, detergents, powders, perfume and cologne, and even as flavoring agents. For example, mercaptans are commonly used in perfumes and cleaning supplies to impart a lavender scent. In foodstuffs and other products, mercaptan compounds are widely used to reproduce the taste and fragrance associated with black currant or grapefruit.

The variety of tastes and flavorings available can be attributed the numerous mercaptan compounds that can be synthesized. Yet, while numerous compounds can be made, economical processes for the production of even relatively simple mercaptans are not available in some cases. In other cases, the purity of known processes require difficult separation steps to obtain mercaptans of a desired purity.

SUMMARY OF THE INVENTION

Embodiments of the invention describe a process for selectively making 2-thiols that includes contacting a linear or branched alpha olefin having at least 5 carbon atoms, $H_2S$, and a catalyst, and reacting the alpha olefin and $H_2S$ in a reactor to produce a reactor effluent comprising a 2-thiol. The catalyst can comprise a support and at least one Group IIIA-VIIIA metal. Suitable branched olefins are branched at the 3-position or higher with respect to the olefin double bond.

In some embodiments, the alpha olefin is selected from the group consisting of alpha olefins having 5 to 18 carbon atoms. In particular embodiments, the alpha olefin is selected from the group consisting of alpha olefins having 5 to 8 carbon atoms. Some suitable alpha olefins include, but are not limited to, 1-pentene, 4-methyl-1-pentene, 1-hexene, 1-heptene, and 1-octene.

In some embodiments the catalyst comprises nickel and molybdenum supported on alumina catalyst or cobalt and molybdenum supported on alumina catalyst. In particular catalysts, the nickel and molybdenum or cobalt and molybdenum are present in the form of oxides, sulfides, or mixtures thereof In some embodiments, the support comprises an alumina, typically gamma alumina. In one embodiment, the catalyst comprises an oxide of cobalt and an oxide of molybdenum supported on alumina.

Some processes described herein selectively produce thiols substituted at the 2-position with respect to the double bond in the olefin. In some processes, a distilled 2-thiol product comprises at least 98 percent by weight of the 2-thiol. In other embodiments, a distilled 2-thiol product may be substantially free of 1-thiol and 3-thiol.

Some embodiments of the invention describe a process for selectively making 2-pentanethiol that includes contacting 1-pentene, $H_2S$, and a catalyst, and reacting the 1-pentene and $H_2S$ in a reactor to produce a reactor effluent comprising a 2-pentanethiol. In further embodiments the catalyst comprises an oxide of cobalt and an oxide of molybdenum supported on alumina or comprises an oxide of nickel and an oxide of molybdenum supported on alumina.

Some particular processes provide a 2-pentanethiol product mixture wherein 1-pentanethiol comprises from 0.01 to about 2% by weight of the composition. Some processes provide a 2-pentanethiol product mixture wherein 3-pentanethiol comprises from 0.01 to about 2% by weight of the composition. Still other processes provide a 2-pentanethiol product mixture that is substantially free of either or both 1-pentanethiol and 3-pentanethiol. In some embodiments, the product mixture is substantially or essentially free of one or more alcohols.

DESCRIPTION OF EMBODIMENTS OF THE INVENTION

In the following description, all numbers disclosed herein are approximate values, regardless whether the word "about" or "approximately" is used in connection therewith. They may vary by up to 1%, 2%, 5%, or sometimes 10 to 20%. Whenever a numerical range with a lower limit, $R_L$, and an upper limit $R_U$, is disclosed, any number R falling within the range is specifically disclosed. In particular, the following numbers R within the range are specifically disclosed: $R=R_L+k*(R_U-R_L)$, where k is a variable ranging from 1% to 100% with a 1% increment, i.e. k is 1%, 2%, 3%, 4%, 5%, ..., 50%, 51%, 52%, ..., 95%, 96%, 97%, 98%, 99%, or 100%. Moreover, any numerical range defined by two numbers, R, as defined above is also specifically disclosed.

All references herein to elements or metals belonging to a certain Group refer to the Periodic Table of the Elements published and copyrighted by CRC Press, Inc., 1999. Also any reference to the Group or Groups shall be to the Group or Groups as reflected in this Periodic Table of the Elements using the IUPAC system for numbering groups. As used herein the term "comprising" is not intended to exclude any additional component, additive or step. For purposes of United States patent practice, the contents of any patent, patent application or publication referenced herein are hereby incorporated by reference in their entirety, especially with respect to the disclosure of synthetic techniques and general knowledge in the art.

Generally, the invention relates to a process for selectively making 2-thiols comprising contacting a linear or branched alpha olefin having at least 5 carbon atoms, $H_2S$, and a catalyst, and reacting the alpha olefin and $H_2S$ in a reactor to produce a reactor effluent comprising a 2-thiol. Additionally, the process relates to a process for selectively making 2-pentanethiol that includes contacting 1-pentene, $H_2S$, and a catalyst; and reacting the 1-pentene and $H_2S$ in a reactor to produce a reactor effluent comprising a 2-pentanethiol. Further embodiments describing the alpha olefins, catalysts, reaction conditions, process conditions and product properties, and other parameters are further described herein.

Catalysts suitable for use in this invention comprise at least one Group IIIA-VIIIA transition metal and a support. Some suitable catalysts are known as sulfactive hydrogenation catalysts or hydrodesulfurization (HDS) catalysts. Such catalysts may include the oxides of Group VIA and Group VIIIA metals such as, but not limited to, cobalt, nickel, molybdenum, iron, tungsten, chromium, and platinum. Alternatively, such catalysts may include the sulfides of Group VIA and Group VIIIA metals such as, but not limited to, cobalt, nickel, molybdenum, iron, tungsten, chromium, and platinum. In yet other embodiments, such catalysts may include the oxides, sulfides, or mixtures thereof, of Group VIA and Group VIIIA metals such as, but not limited to, cobalt, nickel, molybdenum, iron, tungsten, chromium, and platinum. In some embodiments, the catalyst comprises molybdenum. In some embodiments, the catalyst includes two transition metals. In particular embodiments, the catalyst includes cobalt and molybdenum. In other embodiments, the catalyst includes nickel and molybdenum. Some suitable catalysts are available from catalyst manufacturers such as Criterion, Engelhard, Haldor-Topsoe, Akzo, and ChevronTexaco.

Supports suitable for use as a carrier for the transition metal component include any material that is inert to the reaction conditions. Some suitable supports include activated carbon, alumina, zirconia, thoria, pumice, silica and silica-alumina. In some embodiments, the support is alumina. In other embodiments, the support is a gamma alumina. Generally, the support comprises from 50 to 90 percent by weight of the catalyst composition. Alternatively, the support may comprise from 50 to 70 percent by weight of the catalyst composition, alternatively from 60 to 85 percent by weight of the catalyst composition, or alternatively from 70 to 80 percent by weight of the catalyst composition.

Sulfactive hydrogenation catalysts or hydrodesulfurization catalysts comprising at least one Group IIIA-VIIIA transition metal and a support are commercially available. In some embodiments the catalyst comprises a Group IIIA-VIIIA transition metal oxide, a Group IIIA-VIIIA transition metal sulfide, or mixture thereof and a support. Typically, the catalyst may be available in the form of a metal oxide and a support. In some embodiments, the catalyst is partially or completely sulfided prior to use. Alternatively, the catalyst may be employed directly in the oxide form since sulfiding occurs in the presence of $H_2S$ under the reaction conditions.

Generally, the catalyst comprises an oxide of molybdenum and a support. In some embodiments, the catalyst comprises an oxide, sulfide, or mixed oxide/sulfide of molybdenum. In other embodiments, the catalyst comprises an oxide of molybdenum supported on alumina. Typically, the oxide of molybdenum is $MoO_3$. However, other oxides, sulfides or mixed oxides/sulfides of molybdenum may be used. Additionally, other molybdenum compounds, including oxides, sulfides, or mixed oxides/sulfides of molybdenum, which may be converted to $MoO_3$ upon oxidation in oxygen may also be used. While the applicable quantities of the oxide of molybdenum present in the catalyst are stated as weight percent of $MoO_3$, one skilled in the art will recognize that the applicable compositions include other molybdenum materials and the quantities of molybdenum materials which upon oxidation will yield the disclosed quantities of $MoO_3$ described herein. Typically, the catalyst comprises from 5 to 40 weight percent of an oxide of molybdenum; alternatively, from 8 to 35 weight percent; alternatively, from 8 to 15 weight percent; alternatively, from 10 to 20 weight percent; or alternatively, from 15 to 30 weight percent.

In some embodiments, the catalyst comprises an oxide of cobalt, an oxide of molybdenum, and a support. In other embodiments, the catalyst comprises an oxide of cobalt and an oxide of molybdenum supported on alumina. The oxide of molybdenum and the support have been described herein and are generally applicable to the catalyst compositions comprising an oxide of cobalt, an oxide of molybdenum and a support. Some suitable commercially available catalysts are commonly referred to as cobalt molybdate on alumina. Typically, the oxide of cobalt is CoO. However, other cobalt compounds, including oxides, sulfides, or mixed oxides and sulfides of cobalt, which may be converted to CoO upon oxidation in oxygen may also be used. While the applicable quantities of the oxide of cobalt present in the catalyst are stated as weight percent of CoO, one skilled in the art will recognize that the applicable compositions includes other cobalt materials and the quantities of cobalt materials which upon oxidation will yield the disclosed quantities of CoO described herein.

In some embodiments, the catalyst comprising an oxide of cobalt, an oxide of molybdenum, and a support may comprise from 1 to 10 weight percent of an oxide of cobalt. In other embodiments, the catalyst comprising an oxide of cobalt, an oxide of molybdenum, and a support may comprise from 2 to 7 weight percent of an oxide of cobalt; or alternatively, from 3 to 5 weight percent of an oxide of cobalt. In some embodiments, the catalyst comprising an oxide of cobalt, an oxide of molybdenum, and a support comprises from 8 to 35 weight percent $MoO_3$, from 1 to 10 weight percent CoO, and from 50 to 91 percent alumina; alternatively, from 10 to 20 weight percent $MoO_3$, from about 3 to 5 weight percent CoO, and from 75 to 87 percent alumina; or alternatively from 15 to 30 weight percent $MoO_3$, from 3 to 5 weight percent CoO, and from 65 to 82 percent alumina. In further embodiments, the catalyst may also contain from 0.05 to 1 weight percent $Na_2O$. In other embodiments, the catalyst may also contain up to 0.05 weight percent iron. In the embodiment wherein the catalyst also contains iron, the iron may be present as elemental iron or as an oxide.

In some embodiments, the catalyst comprises an oxide of nickel, an oxide of molybdenum and a support. In other embodiments, the catalyst comprises oxides of nickel and an oxide of molybdenum supported on alumina. The oxide of molybdenum and the support have been described herein and are generally applicable to the catalysts comprising an oxide of nickel, an oxide of molybdenum, and a support described herein. Typically, the oxide of nickel is NiO. However, other nickel compounds, including oxides, sulfides, or mixed oxides and sulfides of nickel, which may be converted to NiO upon oxidation in oxygen may also be used. While the applicable quantities of the oxide of nickel present in the catalyst are stated as weight percent of NiO one skilled in the art will recognize that the applicable compositions includes other nickel materials and the quantities of nickel materials which upon oxidation will yield the disclosed quantities of NiO described herein.

In some embodiments, the catalyst comprising an oxide of nickel, an oxide of molybdenum, and a support may comprise from 0.5 to 10 weight percent of an oxide of nickel. In other embodiment, the catalyst comprising an oxide of nickel, an oxide of molybdenum, and a support may comprise from 1 to 7 weight percent of an oxide of nickel; or alternatively, from 2 to 5 weight percent of an oxide of nickel. In other embodiments, the catalyst comprising an oxide of nickel, an oxide of molybdenum, and a support comprises from 8 to 35 weight percent $MoO_3$, from 0.5 to 10 weight percent NiO, and from 55 to 91.5 percent alumina; from 8 to 35 weight percent $MoO_3$, from 1 to 7 weight percent NiO, and from 58 to 91 percent alumina; alternatively, from 15 to 30 weight percent $MoO_3$, from 2 to 5 weight percent NiO, and from 65 to 83 percent alumina; alternatively, from 10 to 20 weight percent $MoO_3$, from 2 to 5 weight percent NiO, and from 75 to 88 percent alumina; or alternatively, from 8 to 15 weight percent $MoO_3$, from 2 to 5 weight percent NiO, and from 80 to 90 percent alumina. In further embodiments, the catalyst may also contain from 0.05 to 1 weight percent $Na_2O$. In yet other embodiments, the catalyst may also contain up to 0.05 weight percent iron. In the embodiment wherein the catalyst also contains iron, the iron may be present as elemental iron or as an oxide.

Catalysts described herein can be used with any desired alpha olefin to produce alkanethiols that are primarily substituted with a thiol group at the β- or 2-position with respect to the position of the double bond in the α-olefin. In some embodiments, the alpha olefins can include alpha olefins having 5–18 carbon atoms. In other embodiments, the alpha olefin can be selected from alpha olefins having 5–8 carbon atoms. Particular alpha olefins include, but are not limited to, 1-pentene, 3-methyl-1-pentene, 4-methyl-1-pentene, 1-hexene, 1-heptene, or 1-octene. In other embodiments, the alpha olefins can include 1-pentene, 1-hexene, 1-heptene, or 1-octene. In yet other embodiments, the alpha olefin is 1-pentene.

The process for making reacting the alpha olefin and $H_2S$ is carried out in a reactor. Generally, the reactor can be any vessel (e.g. a storage tank, tote, container, mixing vessel), length of pipe (e.g. a tee, inlet, injection port, or header), or other suitable apparatus in which the alpha olefin and $H_2S$ react to form a 2-thiol. The processes for converting the alpha olefins to 2-thiols can be conveniently carried out in continuous or batch reactors. One useful reactor type is known as a fixed bed catalytic flow reactor. One parameter that can be controlled in a chemical reactor or process is the ratio of $H_2S$ to alpha olefin. While any ratio may be used, generally the $H_2S$ is present in stoichiometric excess. Various embodiments employ an $H_2S$ to alpha olefin molar ratio ranging from 2:1 to 20:1 or more. In other embodiments, the $H_2S$ to alpha olefin molar ratio ranges from 5:1 to 18:1; or alternatively, ranges from 7:1 to 15:1. In particular embodiments, the $H_2S$ to alpha olefin molar ratio is at least 2:1; alternatively, at least 5:1; alternatively, at least 7:1; alternatively, at least 9:1; alternatively, at least 12:1; or alternatively at least 20:1.

Other reaction parameters that can be controlled include the reaction temperature, the reactor outlet temperature, reactor pressure and feed rate of the reactant mixture with respect to catalyst content of the reactor. Reactor temperatures typically range from 0° C. to 280° C. In some embodiments, the reactor temperature can range from 90° C. to 280° C. In some embodiments, the reaction is carried out at temperatures ranging from 100° C. to 250° C., alternatively from 150° C. to 200° C. In other embodiments, the reaction is carried out at temperatures ranging from 160° C. to 175° C. In some embodiments, the reactor outlet temperature is less than about 280° C.

Generally, the reaction between the alpha olefin and $H_2S$ can occur at any pressure. In some embodiments, the reaction between the alpha olefin and $H_2S$ can occur at a reactor pressure less than 5000 psig. In other embodiments, the reaction between the alpha olefin and $H_2S$ is carried out at a reactor pressure ranging from 120 psig to 800 psig. In other embodiments the reactor pressure can range from 250 to 750 psig, or alternatively, from 400 psig to 475 psig. In other embodiments, the reactor pressure can range from 150 to 500 psig. In yet other embodiments, the reactor pressure is about 100 psig.

The feed rate of the reactant mixture comprising the alpha olefin and the $H_2S$ can be selected according to the parameters of the process. In some embodiments, the feedrate ranges from 0.0001 to 1.0 liter of the reactant mixture per cubic centimeter of the catalyst per hour. In other embodiments, the process is carried out by feeding the reactant mixture at a rate of from 0.0001 to 0.2 liter of the reactant mixture and the hydrogen sulfide per cubic centimeter of the catalyst per hour. In other embodiments the alpha olefin is provided at a weight hourly space velocity ranging from 0.05 to 5; alternatively, from 0.1 to 2.5; alternatively, from 0.1 to 1.5; or alternatively, from 0.1 to 0.5. Weight hourly space velocity is defined as the weight of material processed per weight of catalyst per hour.

Another reaction parameter is the weight average temperature of the reactor. As used herein, the term weight average reactor temperature is half of the difference between the reactor outlet temperature and the reactor inlet temperature, $(T_{out} - T_{in})/2$. In some embodiments, the weight average reactor temperature is selected to control the reaction's selectivity for 2-thiols over other thiols, especially 1-thiols and/or 3-thiols. In some embodiments, the weight average temperature is less than 200° C. In particular embodiments, the weight average temperature is 160° C. to 175° C. A person of ordinary skill in the art understands how to manipulate the weight average reactor temperature for various alpha olefins and various product requirements. For instance, the weight average reactor temperature may be increased or decreased depending on the relative thermodynamic parameters to promote or inhibit the production of various positional isomers, for example 1-thiols and/or 3-thiols, present in the product that otherwise contains primarily 2-thiol. For example, as the catalyst remains online the weight average reactor temperature may be increased to maintain the desired positional isomer selectivity or selectivities.

Generally, the process has a high conversion of alpha olefins. In some embodiments, that conversion of the alpha olefin is greater than 70 mole percent. In other embodiments, the conversion of the alpha olefin is greater than 80 mole percent; alternatively, greater than 85 mole percent; alternatively, greater than 90 mole percent; or alternatively, greater than 95 mole percent.

A product of the process is generally a 2-thiol. Generally, the process proportionally produces increased quantities of 2-thiols from alpha olefin than other processes. In particular, the process produces more 2-thiol than other thiol products (e.g. 1-thiols and/or 3-thiols). In some embodiments, the reactor effluent comprises a molar ratio of 2-thiol to other thiols greater than 5. In other embodiments, the reactor effluent comprises a molar ratio of 2-thiol to other thiols greater than 7; alternatively, greater than 9; or alternatively, greater than 11. In some embodiments, the reactor effluent comprises greater than 65 mole percent 2-thiols. In other embodiments, the reactor effluent comprises greater that 75 mole percent 2-thiols; alternatively, greater than 80 mole percent 2-thiols; or alternatively, greater than 85 mole percent 2-thiol. In further embodiments, the reactor effluent comprises less than 20 percent by mole 3-thiol. In other embodiments, the reactor effluent comprises less than 10 percent by mole 3-thiol; alternatively, less than 5 percent by mole 3-thiol; or alternatively, less than 2 percent by mole 3-thiol. In some embodiments, the reactor effluent comprises less than 10 percent by mole 1-thiol. In yet other embodiments, the reactor effluent comprises less than 8 percent by mole 1-thiol; alternatively, less than 5 percent by mole 1-thiol; alternatively, less than 3 percent by mole 1-thiol; or alternatively, less than 2 percent by mole 1-thiol.

In some embodiments, the weight average reactor temperature can be adjusted to provide a reactor effluent that comprises at least 70 percent by mole 2-thiol. In other embodiments, the weight average reactor temperature can be adjusted to provide a reactor effluent that comprises at least 75 percent by mole 2-thiol; alternatively at least 80 percent by mole 2-thiol, or alternatively at least 85 percent by mole 2-thiol. In further embodiments, the weight average reactor temperature can be adjusted to provide a reactor effluent that comprises less than 20 percent by mole 3-thiol. In other embodiments, the weight average reactor temperature can be adjusted to provide a reactor effluent that comprises less than 10 percent by mole 3-thiol; alternatively, less than 5 percent by mole 3-thiol; or alternatively, less than 2 percent by mole 3-thiol. In further embodiments, the weight average reactor temperature can be adjusted to provide a reactor effluent that comprises less than 10 percent by mole 1-thiol. In other embodiments, the weight average reactor temperature can be adjusted to provide a reactor effluent that comprises less than 8 percent by mole 1-thiol; alternatively, less than 5 percent by mole 1-thiol; alternatively, less than 3 percent by mole 1-thiol; or alternatively, less than 2 percent by mole 1-thiol.

In some embodiments, products having the characteristics described above are obtainable in a single pass through the reactor. In some embodiments, a reactor pressure of 150 to 500 psig is suitable. In some embodiments, the reaction mixture is essentially free of carbon disulfide. As used in this context, the term "essentially free of carbon disulfide" means that no carbon disulfide, except for possible trace impurities present in the other feedstreams, is intentionally added during the reaction process. In some embodiments, carbon disulfide comprises less than 0.01 percent by weight of the reaction mixture.

In some embodiments, the reactor effluent is distilled to remove impurities and produce a distilled 2-thiol product. In some embodiments, the distilled 2-thiol product contains greater than 90 mole percent 2-thiol. In other embodiments, the distilled 2-thiol product contains greater than 92 mole percent 2-thiol; alternatively, greater than 94 mole percent 2-thiol; alternatively, greater than 96 mole percent 2-thiol; alternatively, greater than 97 mole percent 2-thiol; or alternatively, greater than 98 mole percent 2-thiol. In some embodiments, the distilled 2-thiol product is substantially free of products having the thiol group at the 1-position. In other embodiments, the distilled 2-thiol product is substantially free of products having the thiol group at the 3-positions. In yet other embodiments, the distilled 2-thiol product is substantially free of products having the thiol group at the 1- and/or 3-positions. As used in this context the term "substantially free" means that the total content of 1- and/or 3-thiol isomers comprises no more than about 3 percent of the total thiol content of the composition.

In some embodiments, the distilled 2-thiol product comprises from 97 to 100 percent by weight of the 2-thiol. In other embodiments, the distilled 2-thiol product comprises at least 98 percent by weight of the 2-thiol; alternatively, at least 99 percent by weight of the 2-thiol; alternatively, at least 99.5 percent by weight of the 2-thiol; or alternatively, at least 99.99 percent by weight of the 2-thiol. In some distilled 2-thiol products, the distilled 2-thiol product comprises about 97, 98, 99, 99.5, 99.9, or 99.99 weight percent of the total thiol content present in the product mixture. In some embodiments, the distilled 2-thiol product comprises about 97, 98, 99, 99.5, 99.9, or 99.99 weight percent of the amount of 1-, 2-, and 3-thiol content present in the product mixture.

In some embodiments, the distilled 2-thiol product comprises less than 2 weight percent 1-thiol. In other embodiments, the distilled 2-thiol product comprises less than 1 weight percent 1-thiol; or alternatively, less than 0.5 weight percent 1-thiol. In further embodiments, the distilled 2-thiol product comprises from 0.01 to 2 weight percent 1-thiol. In yet other embodiments, the distilled 2-thiol product comprises from 0.01 to 1 weight percent 1-thiol; or alternatively, from 0.01 to 0.5 weight percent 1-thiol.

In other embodiments, the distilled 2-thiol product comprises less than 2 weight percent 3-thiol. In other embodiments, the distilled 2-thiol product comprises less than 1 weight percent 3-thiol; or alternatively, less than 0.5 weight percent 3-thiol. In further embodiments, the distilled 2-thiol product comprises from 0.01 to 2 weight percent 3-thiol. In yet other embodiments, the distilled 2-thiol product comprises from 0.01 to 1 weight percent 3-thiol; or alternatively, from 0.01 to 0.5 weight percent 3-thiol.

In still other embodiments, the composition is substantially free of one or more alcohols that are derived from the alpha olefin. As used in this context the term "substantially free of one or more alcohols" means that the total content of 1-, 2-, and 3-alcohols having the same number of carbon atoms as the product thiol do not comprise more than about 1 percent by weight of the 2-thiol composition. In particular embodiments that are substantially free of alcohols, the product mixture comprises less than 0.5 percent by weight of alcohols; alternatively, less than 0.1 percent by weight of alcohols; alternatively, less than 0.05 percent by weight of alcohols; or alternatively, less than 0.01 percent by weight of alcohols.

In particular embodiments, the alpha olefin is 1-pentene. The 1-pentene embodiments can utilize any catalyst composition or reaction/reactor conditions as described herein to produce a reactor effluent and/or distilled product having the product distributions as described herein. In some embodiments using 1-pentene, the weight average reactor temperature is less than about 200° C. In particular embodiments, the weight average temperature ranges from 160° C. to 175° C. In particular embodiments, the weight average reactor temperature is about 169° C. (336° F.). While any convenient ratio may be used, in one embodiment, the $H_2S$/1-pentene molar ratio can be about 12:1. In other embodiments, the ratio of $H_2S$ to 1-pentene can be about 9:1, 7:1, or 5:1. In other embodiments, the ratio of $H_2S$ to 1-pentene can be at least 2:1; alternatively, at least 5:1; alternatively, at least 7:1; alternatively, at least 9:1; alternatively, at least 12:1; or alternatively at least 20:1. While any suitable pressure can be used, in one embodiment the reactor pressure can be about 400 psig. As discussed above, generally pressures can range from 120 psig to 800 psig. In some embodiments, the reactor pressure range from 250 to 750 psig, or 400 psig to 475 psig. In some embodiments, a reactor pressure of 150 to 500 psig is suitable. In some embodiments, the reaction mixture is essentially free of carbon disulfide. As used in this context, the term "essentially free of carbon disulfide"

means that no carbon disulfide, except for possible trace impurities present in the other feedstreams, is intentionally added during the reaction process.

EXAMPLES

In the examples below, 1-pentene was reacted with $H_2S$ in the presence of a hydrodesulfurization catalyst prepared according to U.S. Pat. No. 3,963,785. The catalyst used in these examples is a Co/Mo catalyst commercially available from Haldor-Topsoe and typically comprises about 3 to 4 percent by weight CoO, about 15 to 16 percent by weight $MoO_3$, about 0.05 to about 1 percent by weight $Na_2O$, about 0.05 percent by weight iron. The remainder of the catalyst composition comprises gamma alumina.

TABLE III

2-Pentanethiol Synthesis Reaction Using TK-554 Catalyst

| | | | | | Product Analyses | | | | |
|---|---|---|---|---|---|---|---|---|---|
| Run Number | WHSV (1-pentene) | $H_2S$/olefin (Mole ratio) | Temperature (° C.) | Temperature (° F.) | 1-pentene (Mole %) | 2-pentanethiol (Mole %) | 3-pentanethiol (Mole %) | 1-1-pentanethiol (Mole %) | Sulfides and Disulfides (Mole %) |
| 1 | 0.3 | 12 | 120 | 248 | 72.33 | 27.67 | 0 | 0 | 0 |
| 2 | 0.3 | 12 | 130 | 266 | 71.44 | 27.99 | 0 | 0.57 | 0 |
| 3 | 0.3 | 12 | 140 | 284 | 61.94 | 36.5 | 0 | 1.56 | 0 |
| 4 | 0.3 | 12 | 160 | 320 | 25.76 | 69.16 | 0 | 3.01 | 2.07 |
| 5 | 0.3 | 12 | 180 | 356 | 1.52 | 86.66 | 4.81 | 3.98 | 3.02 |
| 6 | 0.3 | 12 | 200 | 392 | 1.64 | 80.56 | 9.98 | 5.48 | 2.34 |
| 7 | 0.3 | 12 | 220 | 428 | 2.85 | 70.88 | 18.69 | 7.58 | 0 |
| 8 | 0.3 | 12 | 163 | 325.4 | 19.38 | 75.54 | 0 | 3.29 | 1.79 |
| 9 | 0.3 | 12 | 166 | 330.8 | 13.33 | 80.75 | 0 | 3.73 | 2.2 |
| 10 | 0.3 | 12 | 169 | 336.2 | 9.84 | 83.44 | 0 | 4.19 | 2.53 |
| 11 | 0.3 | 12 | 172 | 341.6 | 2.34 | 88.5 | 1.66 | 4.94 | 2.55 |

While the invention has been described with a limited number of embodiments, these specific embodiments are not intended to limit the scope of the invention as otherwise described and claimed herein. Moreover, variations and modifications therefrom exist. In some embodiments, the 2-thiol products described herein are substantially or essentially free of any compounds not otherwise expressly recited herein. In certain embodiments, the products are free of products resulting from the reaction of carbon disulfide in the presence of the alpha olefin, $H_2S$ and the catalyst. Some embodiments of the invention include additional components such as additives and stabilizers. While the processes are described as comprising one or more steps, it should be understood that these steps can be practiced in any order or sequence unless otherwise indicated. These steps may be combined or separated. Of course additional steps may be included unless otherwise specified. Some processes described herein do not include the addition of hydrogen disulfide. Some embodiments of the invention consist of or consist essentially of the enumerated components of the compositions or enumerated steps of the processes described herein. Finally, any number disclosed herein should be construed to mean approximate, regardless of whether the word "about" or "approximate" is used in describing the number. The appended claims intend to cover all such variations and modifications as falling within the scope of the invention.

What is claimed is:

1. A process for selectively making 2-thiols, comprising:
   a. contacting a linear or branched alpha olefin having at least 5 carbon atoms, $H_2S$, and a catalyst; and
   b. reacting the alpha olefin and $H_2S$ in a reactor to produce a reactor effluent comprising a 2-thiol and having a molar ratio of 2-thiol to other thiols greater than 5;
   wherein the catalyst comprises a support and at least one Group IIIA-VIIIA metal, and
   wherein the contacting is performed essentially free of carbon disulfide.

2. The process of claim 1, wherein the alpha olefin is 1-pentene, 4-methyl-1-pentene, 3-methyl-1-pentene, 1-hexene, 1-heptene, or 1-octane.

3. The process of claim 1, wherein the catalyst comprises molybdenum.

4. The process of claim 3, wherein the catalyst comprises an oxide, sulfide or mixed oxide/sulfide of molybdenum.

5. The process of claim 1, wherein the catalyst comprises an oxide of cobalt and an oxide of molybdenum supported on alumina.

6. The process of claim 1, wherein the catalyst comprises an wade of nickel and an oxide of molybdenum supported on alumina.

7. The process of claim 1 wherein the reactor has a weight average temperature of less than about 200° C.

8. The process of claim 1, wherein the reacting the alpha olefin and $H_2S$ is carried out at a reactor pressure ranging from 120 psig to 800 psig.

9. A process according to claim 1, wherein the alpha olefin is provided at a weight hourly space velocity ranging from 0.05 to 5.

10. The process of claim 1, wherein a molar ratio of $H_2S$ to alpha olefin is at least 5:1.

11. The process of claim 1, further comprising distilling the reactor effluent to produce a distilled 2-thiol product comprising at least 98 weight percent 2-thiol.

12. A process for selectively making 2-pentanethiol, comprising:
   a. contacting 1-pentene, $H_2S$ and a catalyst; and
   b. reacting the 1-pentene and $H_2S$ in a reactor to produce a reactor effluent comprising a 2-pentanethiol and having a 2-pentanethiol to other thiols molar ratio greater than 5;
   wherein the catalyst comprises an oxide of cobalt and an oxide of molybdenum supported on alumina or comprises an oxide of nickel and an oxide of molybdenum supported on alumina, and wherein the contacting is performed essentially free of carbon disulfide.

13. The process of claim 12, herein a molar ratio of $H_2S$ to 1-pentene is at least 5:1.

14. The process of claim 12, further comprising distilling the reactor effluent to produce a distilled 2-pentanethiol product comprising at least 98 weight percent 2-pentanethiol.

15. The process of claim 1, wherein the reactor has a weight average temperature ranging from 160 ° C. to 175° C.

16. The process of claim 1, wherein the alpha olefin is provided to the reactor at a weight hourly space velocity ranging from 0.1 to 0.5.

17. The process of claim 1, wherein the conversion of the alpha olefin is greater than 70 mole percent.

18. The process of claim 12, wherein the reactor has a weight average temperature ranging from 160 ° C. to 175° C.

19. The process of claim 12, wherein 1-pentene is provided to the reactor at a weight hourly space velocity ranging from 0.1 to 0.5.

20. The process of claim 12, wherein the conversion of the 1-pentene is greater than 70 mole percent.

* * * * *